US010125168B2

(12) United States Patent
Kobayashi et al.

(10) Patent No.: US 10,125,168 B2
(45) Date of Patent: Nov. 13, 2018

(54) SYNTHETIC PEPTIDE FOR ADJUSTING BALANCE BETWEEN PRESENCE OF TYPE 1 TNF RECEPTOR AND TYPE 2 TNF RECEPTOR AND USE THEREOF

(71) Applicant: TOAGOSEI CO., LTD., Tokyo (JP)

(72) Inventors: Nahoko Kobayashi, Tsukuba (JP); Tetsuhiko Yoshida, Tsukuba (JP)

(73) Assignee: TOAGOSEI CO. LTD., Tokyo (JP)

( * ) Notice: Subject to any disclaimer, the term of this patent is extended or adjusted under 35 U.S.C. 154(b) by 592 days.

(21) Appl. No.: 14/429,612

(22) PCT Filed: Sep. 20, 2013

(86) PCT No.: PCT/JP2013/075536
§ 371 (c)(1),
(2) Date: Mar. 19, 2015

(87) PCT Pub. No.: WO2014/046247
PCT Pub. Date: Mar. 27, 2014

(65) Prior Publication Data
US 2015/0232512 A1 Aug. 20, 2015

(30) Foreign Application Priority Data
Sep. 20, 2012 (JP) .................. 2012-207419

(51) Int. Cl.
*A61K 38/16* (2006.01)
*C07K 7/08* (2006.01)
*C07K 14/00* (2006.01)
*A61K 38/10* (2006.01)

(52) U.S. Cl.
CPC ............... *C07K 7/08* (2013.01); *A61K 38/10* (2013.01); *A61K 38/16* (2013.01); *C07K 14/001* (2013.01)

(58) Field of Classification Search
None
See application file for complete search history.

(56) References Cited

U.S. PATENT DOCUMENTS

| 9,365,618 B2 * | 6/2016 | Kobayashi | ......... C07K 14/7151 |
| 9,480,727 B2 * | 11/2016 | Kobayashi | ......... A61K 38/1716 |
| 2011/0263835 A1 * | 10/2011 | Ting | ................. C07K 14/51 530/399 |
| 2014/0051647 A1 | 2/2014 | Kobayashi et al. | |

FOREIGN PATENT DOCUMENTS

| JP | 10-500304 A | 1/1998 |
| WO | 95/31206 A1 | 11/1995 |
| WO | 2012/142659 A1 | 10/2012 |
| WO | 2012/150676 A1 | 11/2012 |

OTHER PUBLICATIONS

Goodwin et al. ('Molecular cloning and expression of the type 1 and type 2 murine receptors for tumor necrosis factor' Molecular and Cellular Biology v11(6) Jun. 1991 pp. 3020-3026).*
Lis et al. ('Tumor necrosis factor inhibitors—state of knowledge' Arch Med Sci v10(6) Dec. 2014 pp. 1175-1185) (Year: 2014).*
Correa et al. ('A graph-structural method for prediction of polymer properties' Brazilian Journal of Chemical Engineering v21(4) Oct.-Dec. 2004 pp. 621-628) (Year: 2004).*
Luo, Dianhong et al. "Differential Functions of Tumor Necrosis Factor Receptor 1 and 2 Signaling in Ischemia-Mediated Arteriogensis and Angiogenesis." American Journal of Pathology. vol. 169, No. 5. 2006. pp. 1886-1898.
Nakazawa, Toru, et al. "Tumor Necrosis Factor-a Mediates Photoreceptor Death in a Rodent Model of Retinal Detachment". Investigative Ophthalmology & Visual Science. vol. 52, No. 3. 2011. pp. 1384-1391.
He, Ping, et al. "Deletion of tumor necrosis factor death receptor inhibits amyloid β generation and prevents learning and memory deficits in Alzheimer's mice". Journal of Cell Biology. vol. 178, No. 5. 2007. pp. 829-841.
Al-Lamki, RS, et al. "TNF receptors differentially signal and are differentially expressed and regulated in the human heart". American Journal of Transplantation. vol. 9, No. 12. 2009. pp. 2679-2696.
Marschinke, Franziska, et al. "Dual Effects of TNFa on Nerve Fiber Formation from Ventral Mesencephalic Organotypic Tissue Cultures". Brain Research. vol. 1215. 2008. pp. 30-39.
Chen, Guoqing, et al. "TNF-R1 Signaling: A Beautiful Pathway". Science. vol. 296, No. 5573. 2002. pp. 1634-1635.
Tartaglia, Louis A. et al. "The Two Different Receptors for Tumor Necrosis Factor Mediate Distinct Cellular Responses". Proceedings of the National Academy of Sciences of U.S.A. vol. 88, No. 20. 1991. pp. 9292-9296.
Sato, Masao et al. "Study on TNF a and soluble TNF receptors (p55 and p75) in Knee Joint Fluid from Chronic Rheumatoid Arthritis Patients". Riumachi. vol. 41, No. 2. 2001. p. 426, W43-1.
Naruse, Katsuhiko, et al. "Study on Expression of TNF-R1 and -R2 in Pregnant Women with Pre-eclampsia". Acta Obstetrica et Gynaecologia Japonica. vol. 55, No. 2. 2003. p. 244. P-220.
Hosono, et al. "Analysis of the TNF-alpha, TNF-R1 and TNF R-2 in Colorectal Adenoma". Dai 69 Kai. Proceedings of the Japanese Cancer Association. 2010. p. 335, P-0753.
Mar. 24, 2015 International Preliminary Report on Patentability issued in International Application No. PCT/JP2013/075536.

(Continued)

*Primary Examiner* — Karlheinz R. Skowronek
*Assistant Examiner* — Ronald T Niebauer
(74) *Attorney, Agent, or Firm* — Oliff PLC (57) ABSTRACT

Provided is a method for adjusting the balance of TNF-R1 and TNF-R2 in cells present at a target organ, tissue or site. In the adjustment method provided, when increasing the relative presence of TNF-R2 compared to the presence of TNF-R1 in the cells, a synthetic peptide is supplied to the cells, with the peptide being essentially made of at a TNF-R1 signal peptide motif or a modified amino acid sequence thereof; and when decreasing the relative presence of TNF-R2 compared to the presence of TNF-R1 in the cells, a synthetic peptide is supplied to the cells, with the peptide being essentially made of a TNF-R2 signal peptide motif or a modified amino acid sequence thereof.

3 Claims, 1 Drawing Sheet
Specification includes a Sequence Listing.

(56) References Cited

OTHER PUBLICATIONS

Oct. 5, 2017 Office Action issued in Japanese Patent Application No. 2014-536938.
Furusawa, Takehiko, et al. "Time-dependent Concentration Profile of Blood Cytokines (G-CSF, M-CSF, TNF-R1 and TNF-R2) during Perioperative Period of Open-heart Surgery". Official Publication of the Japaense Society for Cardiovascular Surgery. vol. 30. 2001. p. 325, P-153.

* cited by examiner

SYNTHETIC PEPTIDE FOR ADJUSTING BALANCE BETWEEN PRESENCE OF TYPE 1 TNF RECEPTOR AND TYPE 2 TNF RECEPTOR AND USE THEREOF

TECHNICAL FIELD

The present invention relates to a material and a method for adjusting the balance between the presence of type 1 TNF receptor (TNF-R1) and type 2 TNF receptor (TNF-R2) in the cell membrane of target cells. In particular, it relates to a synthetic peptide used for carrying out the adjustment and use thereof.

The present application claims priority based on Japanese Patent Application No. 2012-207419 filed on Sep. 20, 2012, and its entire contents are incorporated herein by reference.

BACKGROUND ART

Tumor necrosis factors generally called TNF (typically three types, namely TNF-α, TNF-β (LT-α), LT-β) are cytokines that are produced primarily in immune system cells. TNF-α being representative thereof is produced mainly in macrophages and shows various physiological activities such as small thrombi formation and apoptosis induction, etc. Excessive production (expression) of TNF-α is known to bring on diseases such as rheumatoid arthritis and the like.

As for the receptors to which such TNF binds, there are a type 1 TNF receptor (tumor necrosis factor receptor 1 or "TNF-R1" hereinafter) having a molecular weight of about 55 kDa and a type 2 TNF receptor (tumor necrosis factor receptor 2 or "TNF-R2" hereinafter) having a molecular weight of about 75 kDa.

These two types of TNF receptor are known to give rise to different, individual physiological effects. It is reported, for instance, that in a test with TNF-R1 knockout mice and TNF-R2 knockout mice, arteriogenesis of the upper limb and angiogenesis of the lower limb are enhanced in TNF-R1 knockout mice, but are impaired in TNF-R2 knockout mice (Non-Patent Document 1). It has also been reported that the progress of glaucoma is slower in TNF-R2 knockout mice than in wild-type mice (oral presentation by S. McKinnon et al., "Neuroinflammation in Glaucoma" at XIX Biennial Meeting of the International Society for EYE RESEARCH, Jul. 18-23, 2010). It is also reported that photoreceptor degeneration induced by retinal detachment is mediated by TNF-α acting via TNF-R2, but not much affected by TNF-R1 deficiency (Non-Patent Document 2).

CITATION LIST

Non-Patent Literature

[Non-Patent Document 1] American Journal of Pathology, vol. 169(5), 2006, pp. 1886-1898
[Non-Patent Document 2] Investigative Ophthalmology & Visual Science, vol. 52(3), 2011, pp. 1384-1391
[Non-Patent Document 3] Journal of Cell Biology, vol. 178(5), 2007, pp. 829-841

SUMMARY OF INVENTION

As described above, while both being TNF receptors, TNF-R1 and TNF-R2 individually induce different physiological activities. In other words, it suggests that a TNF (e.g. TNF-α) mediates different physiological effects when the TNF binds to TNF-R1 and when it binds to TNF-R2.

Accordingly, if the balance between the presence (e.g. expression) of TNF-R1 and TNF-R2 can be adjusted in a target organ, tissue or site (or more microscopically, in cells present in the organ, tissue or site), it will be possible to bring about (or enhance) the manifestation of a desirable physiological effect in the organ, tissue or site or to disable (or inhibit) the manifestation of an undesirable physiological effect in the organ, tissue or site.

For example, with respect to the reported examples described above, by means of adjusting the ratio of the presence (expression) of TNF receptors present (or expressed) in the cells (cell membrane) of the tissue or site of interest to a greater relative presence (expression) of TNF-R2 than usual, development of arteries and other blood vessels can be enhanced in the tissue or site. As for retinal diseases such as retinal detachment, etc., by adjusting the ratio of the presence (expression) of TNF receptors in retinal photoreceptor cells or ganglion cells to a lower relative presence (expression) of TNF-R2 than usual, apoptosis of the photoreceptor cells and the like can be inhibited.

Non-Patent Document 3 reports that in an experiment with TNF-R1 gene knockout transgenic mice, formation of amyloid 6 was inhibited, resulting in reduced formation of amyloid 6 plaque in the brain. This suggests that the balance between the presence of TNF-R1 and TNF-R2 can be modified in the brain and the relative presence (expression) of TNF-R2 can be specifically increased to allow competitive inhibition of binding of a TNF (primarily TNF-α) to TNF-R1; and as a result, it is expected to make a contribution in treating or improving Alzheimer's disease. In addition, improvement in insulin resistance is also expected with competitive inhibition of binding of a TNF (primarily TNF-α) to TNF-R1.

However, there has hitherto been no method or drug for adjusting the balance between the presence (e.g. expression) of TNF-R1 and TNF-R2 in the cell membrane, easily and highly efficiently.

The present invention has been thus made to provide a method for adjusting the balance between the presence (e.g. expression) of TNF-R1 and TNF-R2 in at least one species of cells present in a desired organ, tissue or site, in vivo or in vitro, and a material (drug composition) used in the method.

To achieve the objectives, the present invention provides a method for adjusting the balance between the presence of type 1 TNF receptor (TNF-R1) and type 2 TNF receptor (TNF-R2) in at least one species of cells that are present in a prescribed target organ, tissue or site and are capable of expressing both TNF-R1 and TNF-R2 (i.e. the quantitative ratio (relative presence) of TNF-R1 and TNF-R2 present typically in the cell membrane of the cells), in vivo (typically, in a human or non-human mammal) or in vitro.

In particular, in the adjustment method disclosed herein, (1) when increasing the relative presence of TNF-R2 compared to the presence of TNF-R1 in the cells present in the prescribed organ, tissue or site, a synthetic peptide is supplied to the cells, with the peptide being essentially consisting of at least one species of TNF-R1 signal peptide motif or an amino acid sequence formed by substituting, deleting and/or adding one or several amino acid residues in/from/to the peptide motif (or a "modified amino acid sequence" of the signal peptide motif, hereinafter).

On the other hand, (2) when decreasing the relative presence of TNF-R2 compared to the presence of TNF-R1 in the cells present in the prescribed organ, tissue or site, a synthetic peptide is supplied to the cells, with the peptide being essentially consisting of at least one species of TNF- R2 signal peptide motif or an amino acid sequence formed by substituting, deleting and/or adding one or several amino acid residues in/from/to the peptide motif (or a "modified amino acid sequence" of the signal peptide motif, hereinafter).

The organ, tissue and site used in the adjustment method of the present invention encompass a cultured organ (possibly a whole organ), cultured tissue and cultured cells (e.g. a culture with dispersed cultured cells, or a cell cluster), respectively, collected from a prescribed organism (typically a human or non-human mammal) to carry out the method in vitro.

The present inventors have come to complete this invention upon their discovery that when various cultured cells are supplied with synthetic peptides consisting of signal peptide motifs of proteins constituting TNF receptors, the signal peptide of TNF-R1 origin and the signal peptide of TNF-R2 origin exert completely different effects on the presence (typically the expression) of TNF-R2.

In other words, according to the adjustment method disclosed herein, by carrying out the process (1), the presence of TNF-R2 can be increased in cells present in a target organ, tissue or site. As a result, the relative presence of TNF-R2 can be increased, compared to the presence of TNF-R1.

According to the adjustment method disclosed herein, by carrying out the process (2), the presence of TNF-R2 can be decreased in cells present in a target organ, tissue or site. As a result, the relative presence of TNF-R2 can be decreased, compared to the presence of TNF-R1.

Thus, according to the adjustment method disclosed herein, the balance between the presence of TNF-R1 and TNF-R2 in target cells can be easily adjusted (controlled) by supplying the cells with a synthetic peptide primarily comprising a TNF-R1 signal peptide motif or a modified amino acid sequence thereof, or a synthetic peptide primarily comprising a TNF-R2 signal peptide motif or a modified amino acid sequence thereof.

Accordingly, the adjustment method disclosed herein can contribute to treat or improve various TNF-mediated diseases and lesions (e.g. various vascular diseases and Alzheimer's disease) under the influence of the balance between the presence of TNF-R1 and TNF-R2, more specifically of the relative presence of TNF-R2 compared to TNF-R1. The adjustment method disclosed herein can be preferably implemented in research and development in fields (e.g. fields related to medicine, pharmacology, genetics, biochemistry, biology; the same applies hereinafter) aimed to improve diseases (disorders) mediated by TNF-R1 and TNF-R2.

For example, by carrying out the process (1) to increase the relative presence of TNF-R2 compared to the presence of TNF-R1, development of arteries and other blood vessels can be enhanced in a tissue or site of interest (including a case where a tissue or cells thus processed in vitro is transplanted).

Also, with respect to retinal diseases such as retinal detachment, etc., by subjecting retinal photoreceptor cells or ganglion cells to the process (2) to decrease the relative presence of TNF-R2 compared to the presence of TNF-R1, apoptosis of the photoreceptor cells and the like can be inhibited.

For another application, by increasing the relative presence of TNF-R2 compared to the presence of TNF-R1 in central nervous system cells in the brain or spinal cord (neurons and/or glial cells constituting the brain or spinal cord as well as neural stem cells prior to differentiation into these cells), binding of a TNF (primarily TNF-α) to TNF-R1 can be competitively inhibited to treat or improve Alzheimer's disease as well.

Thus, in a preferable embodiment of the adjustment method disclosed herein, as the cells of interest, nervous system-constituting cells (typically photoreceptor cells, glial cells, or neural stem cells) are used.

As evident from the description above, the present invention also provides a synthetic peptide used in the adjustment method disclosed herein as well as a composition comprising the synthetic peptide.

In particular, a composition disclosed herein is used for increasing the presence of TNF-R2 in at least one species of cells capable of expressing both TNF-R1 and TNF-R2. The composition comprises a synthetic peptide essentially consisting of at least one species of TNF-R1 signal peptide motif or an amino acid sequence formed by substituting, deleting and/or adding one or several amino acid residues in/from/to the peptide motif, and further comprises a pharmaceutically acceptable carrier. The composition is used for increasing the relative presence of TNF-R2 compared to the presence of TNF-R1 in the cells.

By the use of such a pharmaceutical composition (i.e. the synthetic peptide contained in the composition), the process (1) can be carried out.

Accordingly, as another aspect, the present invention provides a method for increasing the presence of TNF-R2 in at least one species of cells capable of expressing both TNF-R1 and TNF-R2 present in a prescribed organ, tissue or site, in vivo or in vitro, the method characterized by carrying out the process (1) using such a pharmaceutical composition (i.e. the synthetic peptide contained in the composition). The present invention also provides a method for producing cells having an increased presence of TNF-R2, the method characterized by carrying out the process (1) using such a pharmaceutical composition (i.e. the synthetic peptide contained in the composition).

Another composition disclosed herein is used for decreasing the presence of TNF-R2 in at least one species of cells capable of expressing both TNF-R1 and TNF-R2. The composition comprises a synthetic peptide essentially consisting of at least one species of TNF-R2 signal peptide motif or an amino acid sequence formed by substituting, deleting and/or adding one or several amino acid residues in/from/to the peptide motif, and further comprises a pharmaceutically acceptable carrier. The composition is used for decreasing the relative presence of TNF-R2 compared to the presence of TNF-R1 in the cells.

By the use of such a pharmaceutical composition (i.e. the synthetic peptide contained in the composition), the process (2) can be carried out.

Accordingly, as another aspect, the present invention provides a method for decreasing the presence of TNF-R2 in at least one species of cells capable of expressing both TNF-R1 and TNF-R2 present in a prescribed organ, tissue or site, in vivo or in vitro, the method characterized by carrying out the process (2) using such a pharmaceutical composition (i.e. the synthetic peptide contained in the composition). The present invention also provides a method for producing cells having a reduced presence of TNF-R2, the method characterized by carrying out the process (2) using such a pharmaceutical composition (i.e. the synthetic peptide contained in the composition).

In implementing the present invention, the TNF-R1 signal peptide motif is preferably the amino acid sequence of any one of SEQ ID NOS: 1 to 5. By using the TNF-R1 signal peptide motif of human (SEQ ID NO: 1), mouse (SEQ ID NO: 2), rat (SEQ ID NO: 3), bovine (SEQ ID NO: 4) or pig (SEQ ID NO: 5) origin, the process (1) can be preferably carried out.

In implementing the present invention, the TNF-R2 signal peptide motif is preferably the amino acid sequence of any one of SEQ ID NOS: 6 to 8. By using the TNF-R2 signal peptide motif of human (SEQ ID NO: 6), mouse (SEQ ID NO: 7) or rat (SEQ ID NO: 8) origin, the process (2) can be preferably carried out.

The synthetic peptide used in practicing the present invention is preferably a chemically synthesized peptide having a total of 25 or fewer amino acid residues.

DESCRIPTION OF EMBODIMENTS

Preferred embodiments of the present invention are described below. Note that technical matters other than the matters particularly mentioned in the present description (e.g. the primary structure and chain length of a synthetic peptide disclosed herein) which are required for carrying out the present invention (e.g., general matters relating to chemical peptide synthesis, cell cultivation, and preparation of a pharmaceutical composition containing a peptide) are matters of design variation that could be apprehended by a person skilled in the art based on conventional art in such fields as cell engineering, physiology, medicine, pharmacology, organic chemistry, biochemistry, genetic engineering, protein engineering, molecular biology, genetics, and the like. The present invention can be practiced based on the technical details disclosed in the present description and common general technical knowledge in the pertinent fields. In the following description, amino acids are indicated by single-letter designations (in sequence listings, by three-letter designations) in accordance with the nomenclature for amino acids set forth in the IUPAC-IUB guidelines.

The present description incorporates by reference the entire contents of all the documents cited herein.

In the present description, the term "synthetic peptide" refers to a peptide that is manufactured by artificial chemical synthesis or biosynthesis (i.e. genetic engineering-based production).

In this description, the term "peptide" refers to an amino acid polymer having a plurality of peptide bonds, and is not limited by the number of amino acid residues included in the peptide chain, with the term typically referring to one having a relatively small molecular weight with a total of 50 or fewer (e.g. 25 or fewer) amino acid residues.

In this description, unless otherwise specified, the term "amino acid residue" includes the N-terminal amino acid and the C-terminal amino acid of a peptide chain.

In this description, the term "modified amino acid sequence" relative to a selected amino acid sequence refers to an amino acid sequence formed by substituting, deleting and/or adding (inserting) one or several (e.g. two or three) amino acid residues without impairing the function (i.e. the ability to increase or decrease the presence (expression) of TNF-R2) of the selected amino acid sequence. Typical examples of the modified amino acid sequence referred to in the present description include a sequence generated by conservative amino acid replacement where one or several (typically two or three) amino acid residues are conservatively substituted (e.g. a basic amino acid residue is substituted with a different basic amino acid residue; e.g. mutual substitution between a lysine residue and an arginine residue), a sequence corresponding to a selected amino acid sequence with addition (insertion) or deletion of one or several (typically two or three) amino acid residues, and the like.

Hence, in the concepts of the synthetic peptide (or "TNF-R2 upregulating peptide" hereinafter) to increase the presence of TNF-R2 or the synthetic peptide (or "TNF-R2 downregulating peptide" hereinafter) to decrease the presence of TNF-R2 used in the adjustment method disclosed herein, there are included a synthetic peptide consisting of the same amino acid sequence as each corresponding SEQ ID NO described below as well as a synthetic peptide consisting of a modified amino acid sequence formed by substituting (e.g. conservatively substituting as described above), deleting and/or adding one or several (typically two or three) amino acid residues in/from/to the amino acid sequence of the each corresponding SEQ ID NO, with the modified amino acid sequence having a similar activity to increase or decrease the presence of TNF-R2 and being capable of adjusting the balance between the presence of TNF-R1 and TNF-R2.

In this description, the term "polynucleotide" refers to a polymer (nucleic acids) in which several nucleotides are linked by phosphodiester bonds, but not limited by the number of nucleotides. As used herein, the term 'polynucleotide' encompasses DNA fragments and RNA fragments of various lengths.

The composition used in the adjustment method disclosed herein comprises the TNF-R2 upregulating peptide or TNF-R2 downregulating peptide as an active ingredient.

As described above, the TNF-R2 upregulating peptide disclosed herein can be perceived as a synthetic peptide that does not exist in nature in view that it is a synthetic peptide essentially consisting of a TNF-R1 signal peptide motif or a modified amino acid sequence thereof. Similarly, the TNF-R2 downregulating peptide can be perceived as a synthetic peptide that does not exist in nature in view that it is a synthetic peptide essentially consisting of a TNF-R2 signal peptide motif or a modified amino acid sequence thereof.

Table 1 shows preferable examples of an amino acid sequence constituting the TNF-R2 upregulating peptide or TNF-R2 downregulating peptide disclosed herein.

TABLE 1

| No. | Amino acid sequence | Number of total amino acid residues |
|---|---|---|
| 1 | MGLSTVPDLLLPLVLLELLVG (SEQ ID NO: 1) | 21 |
| 2 | MGLPTVPGLLLSLVLLALLMG (SEQ ID NO: 2) | 21 |
| 3 | MGLPIVPGLLLSLVLLALLMG (SEQ ID NO: 3) | 21 |

TABLE 1 -continued

| No. | Amino acid sequence | Number of total amino acid residues |
|---|---|---|
| 4 | MGLPTVPGLLLPLVLPALLAD (SEQ ID NO: 4) | 21 |
| 5 | MGLSTVPGLLLPLVLRALLVD (SEQ ID NO: 5) | 21 |
| 6 | MAPVAVWAALAVGLELWAAAHA (SEQ ID NO: 6) | 22 |
| 7 | MAPAALWVALVFELQLWATGHT (SEQ ID NO: 7) | 22 |
| 8 | MAPAALWVALVVELQLWATGHT (SEQ ID NO: 8) | 22 |

Among these listed amino acid sequences, Nos. 1 to 5 are examples of a TNF-R1 signal peptide motif preferable as the TNF-R2 upregulating peptide. Nos. 6 to 8 are examples of a TNF-R2 signal peptide motif preferable as the TNF-R2 downregulating peptide.

More specifically, the amino acid sequence of SEQ ID NO: 1 is a human TNF-R1 signal peptide motif. The amino acid sequence of SEQ ID NO: 2 is a mouse TNF-R1 signal peptide motif. The amino acid sequence of SEQ ID NO: 3 is a rat TNF-R1 signal peptide motif. The amino acid sequence of SEQ ID NO: 4 is a bovine TNF-R1 signal peptide motif. The amino acid sequence of SEQ ID NO: 5 is a pig TNF-R1 signal peptide motif.

On the other hand, the amino acid sequence of SEQ ID NO: 6 is a human TNF-R2 signal peptide motif. The amino acid sequence of SEQ ID NO: 7 is a mouse TNF-R2 signal peptide motif. The amino acid sequence of SEQ ID NO: 8 is a rat TNF-R2 signal peptide motif.

In the TNF-R2 upregulating peptide and TNF-R2 downregulating peptide disclosed herein, at least one amino acid residue is preferably amidated. Amidation of a carboxyl group in an amino acid residue (typically the C-terminal amino acid residue of the peptide chain) may increase the structural stability (e.g., protease resistance) of the synthetic peptide.

In the synthetic peptide used, the total number of amino acid residues constituting the peptide chain is suitably 50 or fewer, desirably 30 or fewer, for instance, particularly preferably 25 or fewer. In a general TNF-R1 or TNF-R2 signal peptide motif, the number of amino acid residues is within such a range. A peptide consisting of a TNF-R1 or TNF-R2 signal peptide motif or a modified amino acid sequence thereof is preferably used in the adjustment method disclosed herein.

The TNF-R2 upregulating peptide or TNF-R2 downregulating peptide disclosed herein should just comprise, as an essential constituent (primary constituent), a TNF-R1 or TNF-R2 signal peptide motif or a modified amino acid sequence thereof. As long as the physiological activity of interest is not lost, the peptide may comprise other amino acid residue(s) besides the TNF-R1 or TNF-R2 signal peptide motif or the modified amino acid sequence thereof.

Such a short chain peptide can be easily prepared by chemical synthesis. Thus, the TNF-R2 upregulating peptide and TNF-R2 downregulating peptide can be readily provided. Although no particular limitation is imposed on the conformation (spatial structure) of the peptide as long as the activity of interest is exhibited in the environment employed (in vitro or in vivo), a linear or a helical conformation is preferable from the standpoint of the less likelihood of becoming an immunogen (antigen), a preferable peptide has. A peptide having such a conformation is preferable also from the standpoint of the low susceptibility to epitope formation.

It is noted that in the TNF-R2 upregulating peptide and TNF-R2 downregulating peptide disclosed herein, while all amino acid residues are preferably L-amino acids, some or all of the amino acid residues may be substituted with D-amino acids.

The synthetic peptide disclosed herein can be easily manufactured according to conventional chemical synthesis methodologies. For instance, any of conventional solid-phase and liquid-phase synthetic methods can be employed. A preferable solid-phase synthetic method uses Boc (t-butyloxycarbonyl) or Fmoc (9-fluorenylmethoxycarbonyl) as the protecting group for the amino group. For the synthetic peptide disclosed herein, a peptide chain having a desired amino acid sequence and a portion with modification (e.g., C-terminal amidation) can be synthesized by solid-phase synthesis using a commercial peptide synthesizer (which is, for instance, available from PerSeptive Biosystems, Applied Biosystems, etc.).

Alternatively, the TNF-R2 upregulating peptide and TNF-R2 downregulating peptide may be biosynthesized based on genetic engineering techniques. In particular, a polynucleotide (typically a DNA strand) is synthesized so as to have a nucleotide sequence (including the ATG initiation codon) encoding the amino acid sequence of the desired peptide. Then, in accordance with the host cells, a recombinant vector is constructed so as to have an expression gene construct composed of the synthesized polynucleotide (DNA) and various regulatory elements (including promoters, ribosome binding sites, terminators, enhancers, and various cis-elements which control the expression level) to allow expression of the amino acid sequence within the host cells.

By an ordinary technique, this recombinant vector is inserted into prescribed host cells, and the host cells, or tissue or a mass containing these cells are cultured under specific conditions. In this way, the target TNF-R2 upregulating peptide or TNF-R2 downregulating peptide can be expressed and produced intracellularly.

The target TNF-R2 upregulating peptide and TNF-R2 downregulating peptide can be obtained by isolating the peptides from the host cells (from the culture medium if secreted) and purifying them. Methods hitherto used in the art may be directly employed without modification for constructing the recombinant vector and introducing the constructed recombinant vector into the host cell. Because such methods themselves are not distinctive to the present invention, detailed description is omitted.

For example, a fusion protein expression system may be employed to allow efficient large-scale production in host cells. In particular, a gene (DNA) coding for the amino acid sequence of the target TNF-R2 upregulating peptide or TNF-R2 downregulating peptide is chemically synthesized, and the synthesized gene is introduced to a preferred site on a fusion protein expression vector (e.g. GST (glutathione S-transferase) fusion protein expression vectors such as the pET series available from Novagen as well as the pGEX series available from Amersham Bioscience). Host cells (typically, *Escherichia coli*) are then transformed by the vector. The resulting transformant is cultured to produce the target fusion protein. This protein is then extracted and purified. Subsequently, the purified fusion protein is cleaved with a specific enzyme (protease), and the liberated target peptide fragments (the designed TNF-R2 upregulating peptide or TNF-R2 downregulating peptide) are collected by a method such as affinity chromatography. The TNF-R2 upregulating peptide or TNF-R2 downregulating peptide disclosed herein can be produced by using such a fusion protein expression system heretofore known (e.g., the GST/His system available from Amersham Bioscience may be used).

Alternatively, the target peptide may be synthesized in vitro by constructing a template DNA for a cell-free protein synthesis system (i.e. a synthesized gene fragment having a nucleotide sequence that codes for the amino acid sequence of the TNF-R2 upregulating peptide or TNF-R2 downregulating peptide), and employing a cell-free protein synthesis system with use of various compounds (e.g., ATP, RNA polymerase, amino acids, etc.) required for the peptide synthesis. For information concerning cell-free protein synthesis systems, reference may be made to, for example, Shimizu et al., Nature Biotechnology 19, 751-755 (2001), and Madin et al., Proc. Natl. Acad. Sci. USA, 97(2), 559-564 (2000). Based on the technology described in these articles, many corporations have been conducting contract manufacturing of peptides at the time when this application was filed. Also, wheat germ cell-free protein synthesis kits (such as PROTEIOS™ available from Toyobo Co., Ltd. of Japan) are commercially available.

By a heretofore known method, can be easily produced (synthesized) a single-stranded or double-stranded polynucleotide containing a nucleotide sequence encoding the TNF-R2 upregulating peptide or TNF-R2 downregulating peptide disclosed herein and/or a nucleotide sequence complementary thereto. In other words, by selecting a codon corresponding to the respective amino acid residues constituting the designed amino acid sequence, a nucleotide sequence corresponding to the amino acid sequence of the TNF-R2 upregulating peptide or TNF-R2 downregulating peptide can be easily determined and provided. Once the nucleotide sequence is determined, by utilizing a DNA synthesizer, etc., can be easily obtained a polynucleotide (single strand) corresponding to the desired nucleotide sequence. Furthermore, the target double-stranded DNA can be obtained by using the resulting single-stranded DNA as a template and employing various enzymatic synthetic methods (typically PCR).

The polynucleotide provided by the present invention may be in the form of DNA or RNA (mRNA, etc.). The DNA can be provided as a double strand or a single strand. When it is provided as a single strand, it may be a coding strand (sense strand) or an anticoding strand (anti-sense strand) complementary thereto.

The polynucleotide provided by the present invention can be used as a material for constructing a recombinant DNA (expression cassette) for producing the TNF-R2 upregulating peptide or TNF-R2 downregulating peptide in various host cells or in a cell-free protein synthesis system.

The TNF-R2 upregulating peptide or TNF-R2 downregulating peptide disclosed herein can selectively increase or decrease the presence (expression) of TNF-R2, by acting on at least one species of target TNF receptor-expressing cells (typically central or peripheral nervous system cells, immune system cells, vascular cells and other cardiovascular system cells, retinal cells and other ocular cells).

Thus, either one can be preferably used as an active ingredient in a composition (i.e. pharmaceutical composition) used for adjusting the balance between the presence of TNF-R1 and TNF-R2 described earlier. The peptide may be in a salt form as far as the physiological activity is not impaired. For example, it is possible to use an acid salt of the peptide, which can be obtained by adding a commonly used inorganic or organic acid in accordance with an ordinary technique. Alternatively, it can be a different type of salt (e.g. a metal salt). The "synthetic peptide" in this description and in claims encompasses such salts.

The composition disclosed herein for increasing or decreasing the relative presence of TNF-R2 compared to the presence of TNF-R1 may contain various pharmaceutically (medically) acceptable carriers in accordance with the application form, as far as the TNF-R2 upregulating peptide or TNF-R2 downregulating peptide as the active ingredient is maintained physiologically active. Carriers generally used as diluents or excipients in peptide medications are preferred. Although it may suitably vary depending on the intended purpose and application, typical examples include water, physiological buffers and various organic solvents. The carrier may be an aqueous alcohol (ethanol or the like) solution at an appropriate concentration, glycerol, or non-drying oil such as olive oil. Alternatively, it may be a liposome. Examples of secondary ingredients that may be contained in such a composition include various fillers, bulking agents, binders, wetting agents, surfactants, dyes, fragrances and the like.

Typical examples of the form of the composition for increasing or decreasing the relative presence of TNF-R2 compared to the presence of TNF-R1 include liquid formulas, suspensions, emulsions, aerosols, foams, granules, powders, tablets, capsules, ointments, aqueous gels and the like. For injection, etc., it may be formulated as a freeze-dried product or pellets to prepare a drug solution by dissolving it in saline or a suitable buffer (e.g., PBS) just prior to use.

The process itself of preparing a composition (drug) in various forms with the TNF-R2 upregulating peptide or TNF-R2 downregulating peptide (primary ingredient) and various carriers (secondary ingredients) may be carried out in accordance with a heretofore known method. Because such a preparation process itself is not distinctive to the present invention, detailed description is omitted. The detail information regarding formulations can be found in, for example, Comprehensive Medicinal Chemistry, edited by Corwin Hansch and published by Pergamon Press (1990). The entire contents of this book are incorporated in this description by reference.

The target organ, tissue or site to which the adjustment method of the present invention is applied is not particularly limited as long as there are cells capable of expressing TNF-R2 in addition to TNF-R1 in the target. For instance, the present invention can be applied to cells (e.g. neurons, glial cells) of the central nervous system such as the brain and spinal cord or of the peripheral nervous system, immune system cells (e.g. various lymphocytes, macrophages, neutrophils, eosinophils, basophils, monocytes), cells of the cardiovascular system including blood vessels (e.g. cardiac myocytes constituting the heart, vascular endothelial cells), retinal cells, and so on.

Alternatively, the present invention can be applied to carcinoma cells (tumor cells) in various cancers (tumors).

Alternatively, the present invention can be applied to stem cells including ES cells (embryotic stem cells), iPS cells (induced pluripotent stem cells), adipose stem cells, mesenchymal stem cells such as cartilage stem cells, hematopoietic stem cells, neural stem cells, and so on.

The TNF-R2 upregulating peptide or TNF-R2 downregulating peptide (or the composition comprising one of these) disclosed herein can be used according to a method and dosage appropriate for the form and purpose.

For example, with respect to cells (a cell cluster), tissue or an organ under in vitro incubation, the peptide of interest can be supplied to a culture medium containing the target cultured cells (cultured tissue or organ). Its amount and the number of portions to be added are not particularly limited as they may vary in accordance with the conditions such as the type of cultured product, cell density (initial cell density at the incubation start), passage number, incubation conditions, type of culture medium, etc. When human or non-human mammalian cells, tissue and the like are cultured, it can be added in one to several portions so that the concentration of the peptide in the culture medium is within a range of about 0.1 µM to 100 µM or more preferably within a range of 0.5 µM to 20 µM (e.g., 1 µM to 10 µM).

By supplying the TNF-R2 upregulating peptide or TNF-R2 downregulating peptide disclosed herein to an in vitro culture system, the relative presence of TNF-R2 compared to TNF-R1 can be adjusted in the culture system.

Alternatively, for in vivo adjustment of the relative presence of TNF-R2 compared to TNF-R1 in a prescribed organ, tissue or site (or a tissue fragment or cell cluster transplanted in a prescribed site), that is, for increasing the presence of TNF-R2 to amplify the relative presence of TNF-R2 compared to the presence of TNF-R1, a suitable amount of a TNF-R2 upregulating peptide can be prepared into a liquid formula and administered in a desirable amount to the patient (i.e. in vivo) by intravenous, intramuscular, subcutaneous, intradermal, or intraperitoneal injection. On the other hand, for decreasing the presence of TNF-R2 to reduce the relative presence of TNF-R2 compared to the presence of TNF-R1, a suitable amount of a TNF-R2 downregulating peptide can be similarly administered.

Alternatively, it can be administered directly to the prescribed tissue (i.e., cells constituting the tissue) in a solid form such as tablets, etc., in a gel form such as ointment, etc., or in an aqueous gel form. The amount and the number of portions to be added are not particularly limited as they may vary depending on conditions such as the type of cells subjected to balance adjustment for their presence, the site, organ or tissue where the cells are present, etc.

As described above, in the method disclosed herein for adjusting the balance between the presence of TNF-R1 and TNF-R2, either the process (1) or the process (2) can be carried out. Alternatively, in accordance with the purpose or stages, the process (1) and process (2) can be suitably combined while being carried out in different stages for adjusting the relative presence of TNF-R2 compared to TNF-R1.

Several worked examples related to the present invention are described below while these examples are not intended to limit the scope of the invention.

Example 1: Peptide Synthesis

By solid-phase synthesis (Fmoc chemistry), using a commercial peptide synthesizer (an Intavis AG system) in accordance with the operation manual, the following peptides were synthesized: a synthetic peptide (TNF-R2 upregulating peptide) consisting of the amino acid sequence of SEQ ID NO: 1 shown in Table 1, a synthetic peptide (TNF-R2 upregulating peptide) consisting of the amino acid sequence of SEQ ID NO: 2, a synthetic peptide (TNF-R2 upregulating peptide) consisting of the amino acid sequence of SEQ ID NO: 5, a synthetic peptide (TNF-R2 downregulating peptide) consisting of the amino acid sequence of SEQ ID NO: 6, and a synthetic peptide (TNF-R2 downregulating peptide) consisting of the amino acid sequence of SEQ ID NO: 7. The respective synthetic peptides are referred to as Samples 1, 2, 5, 6 and 7 corresponding to their SEQ ID NOS. These are chemically synthesized linear peptides each formed of a total of 21 (TNF-R2 upregulating peptides of Samples 1, 2, 5) or 22 (TNF-R2 downregulating peptides of Samples 6, 7) amino acid residues. Because the mode of using the peptide synthesizer itself is not distinctive to the present invention, detailed description is omitted.

Example 2: Test of Each Synthetic Peptide for TNF-R2 Upregulating or Downregulating Activity with Cell Line of Mouse Origin The activities of the peptides of Sample 1 and Sample 6 synthesized in Example 1 above were tested with cultured cells of a mouse spinal cord, neuroblastoma cell line (Neuro 2a). The control group was supplied with no peptides. The test details are described below.

Firstly, each peptide synthesized in Example 1 above was dissolved in PBS (phosphate buffered saline) to prepare a stock solution having a peptide concentration of 1 mM (with a small amount of dimethyl sulfoxide (DMSO)).

The Neuro 2a cell line was then seeded in a culture dish of 6 cm diameter at a density of $8.5 \times 10^4$ cells/mL and incubated overnight in a general DMEM culture medium (with 10% FBS, 1% penicillin) at 37° C. in a $CO_2$ incubator at 5% $CO_2$.

After incubated overnight, the culture medium was replaced with a DMEM culture medium containing 2% FBS, 20 µM retinoic acid and 1% penicillin. Incubation was carried on for seven days under the same conditions to effect retinoic acid induction. Subsequently, the culture medium was replaced with a DMEM culture medium containing the TNF-R2 upregulating peptide of Sample 1 or TNF-R2 downregulating peptide of Sample 6 in an amount equivalent to 5 µM, in addition to 2% FBS, 20 µM retinoic acid and 1% penicillin (also containing 12.5 µL of DMSO at this point). Incubation was carried on under the same conditions for two days. The control group (group supplied with no peptide) was incubated for two days in a DMEM culture medium (with 2% FBS, 20 µM retinoic acid, 1% penicillin) supplied only with the aforementioned amount of DMSO, without any added peptide.

After completion of the incubation, cultured cells in each test group were collected and divided into certain test tubes in fractions having the same number of cells. By the immunofluorescence technique described below, the change in the balance between the presence of TNF-R1 and TNF-R2 was then assessed in each test group (group supplied with TNF-R2 upregulating peptide, group supplied with TNF-R2 downregulating peptide).

More specifically, in each test group, for the TNF-R1 measurement, an anti-TNF-R1 rabbit polyclonal antibody (a Santa Cruz Biotechnology, Inc. product, SC-7895) was added to the respective test tubes to a final concentration of $4 \times 10^{-3}$ mg/mL and incubation was carried out at 37° C. for a prescribed time period. As a secondary antibody, a goat anti-rabbit IgG antibody (an Invitrogen product, A11034) labeled with a fluorescent dye (Alexa® 488) was added to the test tubes to a final concentration of $2 \times 10^{-3}$ mg/mL and incubation was carried out at 37° C. for a prescribed time period.

On the other hand, as for the TNF-R2 measurement, an anti-TNF-R2 goat polyclonal antibody (a Santa Cruz Biotechnology, Inc. product, SC-1074) was added to the respective test tubes to a final concentration of $4 \times 10^{-3}$ mg/mL and incubation was carried out at 37° C. for a prescribed time period. As a secondary antibody, a donkey anti-goat IgG antibody (an Invitrogen product, A11055) labeled with a fluorescent dye (Alexa® 488) was added to the test tubes to a final concentration of $4 \times 10^{-3}$ mg/mL and incubation was carried out at 37° C. for a prescribed time period.

Figure 1:
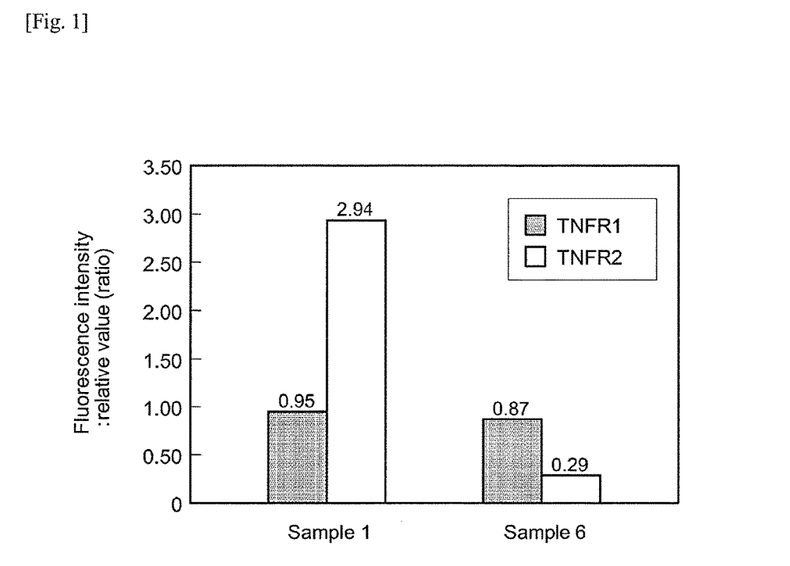
FIG. 1 shows a graph plotting the results of assessment of the balance between the presence of TNF-R1 and TNF-R2 in cultured cells of mouse origin based on immunofluorescence assays using an anti-TNF-R1 polyclonal antibody and an anti-TNF-R2 polyclonal antibody (primary antibodies) along with a fluorescent dye-labeled secondary antibody.

The fluorescence intensities of cells were measured with a flow cytometer (a Millipore system product, Guava® easyCyte 8HT). The results are shown in FIG. 1. For both TNF-R1 and TNF-R2, the fluorescence intensities are shown as relative values with the fluorescence intensities of TNF-R1 and TNF-R2 in the control group (group supplied with no peptide) being 1, respectively.

As shown in FIG. 1, when the mouse cell line (Neuro 2a) was supplied with the TNF-R2 upregulating peptide (TNF-R1 signal peptide) of Sample 1, the presence (expression) of TNF-R2 significantly increased while no significant change was observed in the presence of TNF-R1. By this, the relative presence of TNF-R2 was significantly increased, compared to TNF-R1.

On the other hand, when the mouse cell line (Neuro 2a) was supplied with the TNF-R2 downregulating peptide (TNF-R2 signal peptide) of Sample 6, the presence (expression) of TNF-R2 significantly decreased while no significant change was observed in the presence of TNF-R1. By this, the relative presence of TNF-R2 was significantly decreased, compared to TNF-R1.

As evident from this test, it was found out that by the proper use of the TNF-R2 upregulating peptide and TNF-R2 downregulating peptide disclosed herein, the balance between the presence of TNF-R1 and TNF-R2 could be adjusted in a cell species of interest.

Example 3: Test of Each Synthetic Peptide for TNF-R2 Upregulating or Downregulating Activity with Cell Line of Human Origin The activities of the respective peptides synthesized in Example 1 above were tested with cultured cells of a human neuroblastoma cell line (SK-N-SH). The control group was supplied with no peptides. The test details are described below.

Firstly, each peptide synthesized in Example 1 above was dissolved in DMSO to prepare a stock solution having a peptide concentration of 4 mM.

The SK-N-SH cell line was then seeded in a 4 mL fraction in a culture dish of 6 cm diameter at a density of $1.5 \times 10^5$ cells/mL and incubated overnight in a general DMEM culture medium (with 10% FBS (a Hyclone product, KSD), 2 mM L-glutamine, 50 unit/mL penicillin, and 50 µg/mL streptomycin) at 37° C. in a $CO_2$ incubator at 5% $CO_2$. Due to a low cell density, incubation was carried on for one more days.

After incubated over two nights, the culture medium was replaced with a fresh DMEM culture medium (with 2% FBS, 20 µM retinoic acid, 2 mM L-glutamine, 50 unit/mL penicillin, and 50 µg/mL streptomycin). Incubation was carried on for five days under the same conditions to effect retinoic acid induction.

Subsequently, the culture medium was replaced with a DMEM culture medium containing a peptide (TNF-R2 upregulating peptide or TNF-R2 downregulating peptide) in an amount equivalent to 5 µM, in addition to 2% FBS, 20 µM retinoic acid, 2 mM L-glutamine, 50 unit/mL penicillin and 50 µg/mL streptomycin (also containing 5 µL of DMSO at this point). Incubation was carried on under the same conditions for two days.

The control group (group supplied with no peptide) was incubated for two days in a DMEM culture medium (with 2% FBS, 20 µM retinoic acid, 20 µM retinoic acid, 2 mM L-glutamine, 50 unit/mL penicillin, and 50 µg/mL streptomycin) supplied only with the aforementioned amount of DMSO, without any added peptide.

After completion of the incubation, cultured cells in each test group were collected and divided into certain test tubes in fractions having the same number of cells. By the immunofluorescence technique described below, the change in the balance between the presence of TNF-R1 and TNF-R2 was then assessed in each test group (group supplied with TNF-R2 upregulating peptide, group supplied with TNF-R2 downregulating peptide).

More specifically, in each test group, for the TNF-R1 measurement, an anti-TNF-R1 mouse polyclonal antibody (a Santa Cruz Biotechnology Inc. product, SC-52739) was added to the respective test tubes to a final concentration of $2 \times 10^{-3}$ mg/mL and incubation was carried out under ice-cold conditions for a prescribed time period. As a secondary antibody, a goat anti-mouse IgG antibody (an Invitrogen product, A10029) labeled with a fluorescent dye (Alexa® 488) was added to the test tubes to a final concentration of $4 \times 10^{-3}$ mg/mL and incubation was carried out under ice-cold conditions for a prescribed time period.

On the other hand, as for the TNF-R2 measurement, an anti-TNF-R2 goat polyclonal antibody (a Santa Cruz Biotechnology Inc. product, SC-1074) was added to the respective test tubes to a final concentration of $4 \times 10^{-3}$ mg/mL and incubation was carried out under ice-cold conditions for a prescribed time period. As a secondary antibody, a donkey anti-goat IgG antibody (an Invitrogen product, A21447) labeled with a fluorescent dye (Alexa® 647) was added to the test tubes to a final concentration of $4 \times 10^{-3}$ mg/mL and incubation was carried out under ice-cold conditions for a prescribed time period.

Figure 2:
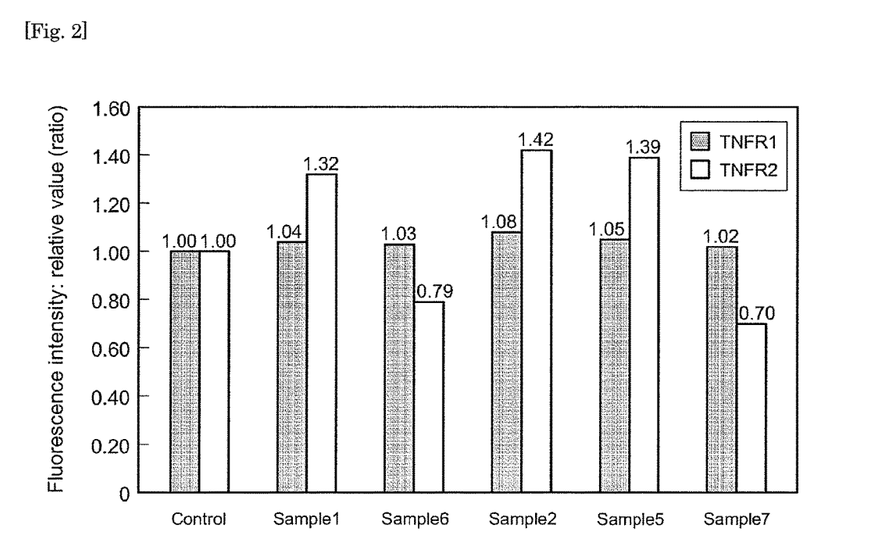
FIG. 2 shows a graph plotting the results of assessment of the balance between the presence of TNF-R1 and TNF-R2 in cultured cells of human origin based on immunofluorescence assays using an anti-TNF-R1 polyclonal antibody and an anti-TNF-R2 polyclonal antibody (primary antibodies) along with a fluorescent dye-labeled secondary antibody.

In the same manner as Example 2 above, the fluorescence intensities of cells were measured with a flow cytometer. The results are shown in FIG. 2. For both TNF-R1 and TNF-R2, the fluorescence intensities are shown as relative values with the fluorescence intensities of TNF-R1 and TNF-R2 in the control group (group supplied with no peptide) being 1, respectively.

As shown in FIG. 2, when the human cell line (SK-N-SH) was supplied with the TNF-R2 upregulating peptide (TNF-R1 signal peptide) of Sample 1, Sample 2 or Sample 5, the presence (expression) of TNF-R2 significantly increased while no significant change was observed in the presence of TNF-R1. By this, the relative presence of TNF-R2 was significantly increased, compared to TNF-R1.

On the other hand, when the human cell line (SK-H-SH) was supplied with the TNF-R2 downregulating peptide (TNF-R2 signal peptide) of Sample 6 or Sample 7, the presence (expression) of TNF-R2 significantly decreased while no significant change was observed in the presence of TNF-R1. By this, the relative presence of TNF-R2 was significantly decreased, compared to TNF-R1.

As evident from these results, it was found out that by the proper use of the TNF-R2 upregulating peptide and TNF-R2 downregulating peptide disclosed herein, the balance between the presence of TNF-R1 and TNF-R2 could be adjusted in various cell species.

Example 4: Preparation of Granular Formulation 50 mg of each synthetic peptide (TNF-R2 upregulating peptide or TNF-R2 downregulating peptide), 50 mg of a crystalline cellulose and 400 mg of lactose were mixed. The mixture was kneaded with 1 mL of an ethanol and water mixture. The kneaded mixture was granulated by a conventional method to obtain a granular formulation (granular composition) comprising the TNF-R2 upregulating peptide or TNF-R2 downregulating peptide disclosed herein as the primary ingredient.

INDUSTRIAL APPLICABILITY

As described above, according to the present invention, the balance between the presence of TNF-R1 and TNF-R2 can be adjusted in cells present in a target organ, tissue or site. Accordingly, the present invention can contribute to treat or improve various TNF-mediated diseases and lesions that are under the influence of the relative presence of TNF-R2 compared to TNF-R1. The present invention can be preferably implemented also in research and development in fields aimed to improve diseases (disorders) mediated by TNF-R1 and TNF-R2.

[Sequence Listing Free Text]

Sequence Listing

TG13-005PCT ST25.txt

The invention claimed is:

1. A method for adjusting the balance between the presence of type 1 TNF receptor (TNF-R1) and type 2 TNF receptor (TNF-R2) in retinal cells, carcinoma cells, stem cells, or at least one species of cells present in the nervous system, the immune system, or the cardiovascular system, the method comprising:

(1) when increasing the relative presence of TNF-R2 compared to the presence of TNF-R1 in the cells, an artificially synthesized peptide is supplied to the cells, the peptide consisting essentially of at least one TNF-R1 signal peptide motif having an amino acid sequence represented by any one of SEQ ID NOs: 1 to 5; or (2) when decreasing the relative presence of TNF-R2 compared to the presence of TNF-R1 in the cells, an artificially synthesized peptide is supplied to the cells, the peptide consisting essentially of at least one TNF-R2 signal peptide motif having an amino acid sequence represented by any one of SEQ ID NOs: 6 to 8.

2. The method according to claim 1, wherein the synthesized peptide has a total of 25 or fewer amino acid residues.

3. The method according to claim 1, wherein the cells are nervous system cells.

* * * * *

```
                          SEQUENCE LISTING

<160> NUMBER OF SEQ ID NOS: 8

<210> SEQ ID NO 1
<211> LENGTH: 21
<212> TYPE: PRT
<213> ORGANISM: Homo sapiens

<400> SEQUENCE: 1

Met Gly Leu Ser Thr Val Pro Asp Leu Leu Pro Leu Val Leu Leu
1               5                   10                  15

Glu Leu Leu Val Gly
            20

<210> SEQ ID NO 2
<211> LENGTH: 21
<212> TYPE: PRT
<213> ORGANISM: Mus musculus

<400> SEQUENCE: 2

Met Gly Leu Pro Thr Val Pro Gly Leu Leu Leu Ser Leu Val Leu Leu
1               5                   10                  15

Ala Leu Leu Met Gly
            20

<210> SEQ ID NO 3
<211> LENGTH: 21
<212> TYPE: PRT
<213> ORGANISM: Rattus norvegicus

<400> SEQUENCE: 3

Met Gly Leu Pro Ile Val Pro Gly Leu Leu Leu Ser Leu Val Leu Leu
1               5                   10                  15

Ala Leu Leu Met Gly
            20

<210> SEQ ID NO 4
<211> LENGTH: 21
<212> TYPE: PRT
<213> ORGANISM: Bos taurus

<400> SEQUENCE: 4

Met Gly Leu Pro Thr Val Pro Gly Leu Leu Leu Pro Leu Val Leu Pro
1               5                   10                  15

Ala Leu Leu Ala Asp
            20

<210> SEQ ID NO 5
<211> LENGTH: 21
<212> TYPE: PRT
<213> ORGANISM: Sus scrofa
```

```
<400> SEQUENCE: 5

Met Gly Leu Ser Thr Val Pro Gly Leu Leu Pro Leu Val Leu Arg
1               5                   10                  15

Ala Leu Leu Val Asp
            20

<210> SEQ ID NO 6
<211> LENGTH: 22
<212> TYPE: PRT
<213> ORGANISM: Homo sapiens

<400> SEQUENCE: 6

Met Ala Pro Val Ala Val Trp Ala Ala Leu Ala Val Gly Leu Glu Leu
1               5                   10                  15

Trp Ala Ala His Ala
            20

<210> SEQ ID NO 7
<211> LENGTH: 22
<212> TYPE: PRT
<213> ORGANISM: Mus musculus

<400> SEQUENCE: 7

Met Ala Pro Ala Ala Leu Trp Val Ala Leu Val Phe Glu Leu Gln Leu
1               5                   10                  15

Trp Ala Thr Gly His Thr
            20

<210> SEQ ID NO 8
<211> LENGTH: 22
<212> TYPE: PRT
<213> ORGANISM: Rattus norvegicus

<400> SEQUENCE: 8

Met Ala Pro Ala Ala Leu Trp Val Ala Leu Val Val Glu Leu Gln Leu
1               5                   10                  15

Trp Ala Thr Gly His Thr
            20
```